US008642764B1

(12) United States Patent
Thimmaiah et al.

(10) Patent No.: US 8,642,764 B1
(45) Date of Patent: Feb. 4, 2014

(54) JULOLIDINE CONJUGATES AND METHODS FOR THEIR PREPARATION AND USE

(75) Inventors: Govindaraju Thimmaiah, Bangalore (IN); Debabrata Maity, Bangalore (IN); Swapan Kumar Pati, Bangalore (IN); Tapas Kumar Kundu, Bangalore (IN); Arun Kumar Manna, Bangalore (IN); Karthigeyan Dhanasekaran, Bangalore (IN)

(73) Assignee: Jawaharlal Nehru Centre for Advanced Scientific Research, Jakkur, Bangalore (IN)

(*) Notice: Subject to any disclaimer, the term of this patent is extended or adjusted under 35 U.S.C. 154(b) by 0 days.

(21) Appl. No.: 13/597,323

(22) Filed: Aug. 29, 2012

(51) Int. Cl.
*C07D 221/22* (2006.01)
*C07D 221/06* (2006.01)
*C07D 451/00* (2006.01)
*C07D 453/00* (2006.01)
*C07D 455/00* (2006.01)

(52) U.S. Cl.
USPC .............................................. 546/94; 546/79

(58) Field of Classification Search
CPC .... A61K 31/44; C07D 451/00; C07D 453/00; C07D 455/00
See application file for complete search history.

(56) References Cited

FOREIGN PATENT DOCUMENTS

WO  WO2010/078333 A2  7/2010

OTHER PUBLICATIONS

Kramer, R. Fluorescent Chemosensors for Cu2+ Ions: Fast, Selective, and Highly Sensitive. Angewandte Chemie International Edition. 1998, vol. 37, p. 772.*
Smith, Pas. et al. Preparation and Properties of Some Substituted Julolidines. Journal of Organic Chemistry. 1952, vol. 17(9), p. 1281, first paragraph, lines 1-10.*
Maity, D. et al. Highly Selective Visible and Near-IR Sensing of Cu2+ Based on Thiourea-Salicylaldehyde Coordination in Aqueous Media. Chemistry a European Journal. 2011, vol. 17, p. 1411.*
Arnesano et al., Perspective in Inorganic Structural Genomics: A Trafficking Route for Copper, *European Journal of Inorganic Chemistry* (Apr. 6, 2004), 2004(8):1583-1593 (Abstract).
Barceloux et al., Copper, *J Toxicol Clin Toxicol.* (1999), 37(2):217-230(Abstract).
Barnham et al., Neurodegenerative diseases and oxidative stress, *Nature Reviews Drug Discovery* (Mar. 2004), 3:205-214 (Abstract).
Barnham et al., Metals in Alzheimer's and Parkinson's Diseases, *Current Opinion in Chemical Biology* (Apr. 18, 2008), 12(2):222-228 (Abstract).
Brewer, Copper in Medicine, *Current Opinion in Chemical Biology* (Feb. 22, 2003), 7(2):207-212 (Abstract).

Brown et al., Biological inorganic and bioinorganic chemistry of neurodegeneration based on prion and Alzheimer disease, *Dalton Transactions* (May 11, 2004), 13:1907-1917 (Abstract).
Burdette et al., ICCC34—golden edition of coordination chemistry reviews. Coordination chemistry for the neurosciences, *Coordination Chemistry Reviews* (Dec. 2000), 216-217:333-361.
Crichton et al., Metal based neurodegenerative diseases—From molecular mechanisms to therapeutic strategies, *Coordination Chemistry Reviews* (Oct. 24, 2007), 252(10-11):1189-1199 (Abstract).
de Silva et al., Signaling Recognition Events with Fluorescent Sensors and Switches, *Chemical Reviews* (Aug. 5, 1997), 97(5):1515-1566 (Abstract).
Domaille et al., Synthetic fluorescent sensors for studying the cell biology of metals, *Nature Chemical Biology* (Feb. 15, 2008, corrected online Jun. 26, 2008), 4:168-175 (Abstract).
Fabbrizzi et al., Sensors and switches from supramolecular chemistry, *Chemical Society Reviews* (1995), 24(3):197-202 (Abstract).
Gaggelli et al., Copper Homeostasis and Neurodegenerative Disorders (Alzheimer's, Prion, and Parkinson's Diseases and Amyotrophic Lateral Sclerosis), *Chemical Reviews* (Jun. 1, 2006), 106(6):1995-2044 (Abstract).
Grandini et al., Exploiting the Self-Assembly Strategy for the Design of Selective CuII Ion Chemosensors, *Angewandte Chemie International Edition* (Oct. 18, 1999), 38(20):3061-3064 (Abstract).
Kim et al., Mechanisms for copper acquisition, distribution and regulation, *Nature Chemical Biology* (Feb. 15, 2008), 4:176-185 (Abstract).
Krämer, Fluorescent Chemosensors for $Cu^{2+}$ Ions: Fast, Selective, and Highly Sensitive, *Angewandte Chemie International Edition* (Dec. 17, 1998), 37(6):772-773 (Abstract).
Küpper et al., Heavy metal uptake by plans and cyanobacteria, *Met Ions Biol Syst.* (2005), 44:97-144 (Abstract).
Leach et al., Trace elements and prion diseases: a review of the interactions of copper, manganese and zinc with the prion protein, *Animal Health Research Reviews* (Mar. 28, 2007), 7:97-105 (Abstract).
Maity et al., Visible—Near-Infrared and Fluorescent Copper Sensors Based on Julolidine Conjugates: Selective Detection and Fluorescence Imaging in Living Cells, *Chem. Eur. J.* (Sep. 1, 2011), 17(40):11152-11161.
Maity et al., Highly Selective Visible and Near-IR Sensing of $Cu^{2+}$ Based on Thiourea-Salicylaldehyde Coordination in Aqueous Media, *Chem. Eur. J.* (Jan. 5, 2011), 17(7):1410-1414.
Martinez-Manez et al., Fluorogenic and Chromogenic Chemosensors and Reagents for Anions, *Chemical Reviews* (2003), 103(Part 11): 4419-4476 (Abstract).
McQuade et al., Conjugated Polymer-Based Chemical Sensors, *Chem. Rev.* (Jun. 9, 2000), 100:2537-2574.
Millhauser, Copper Binding in the Prion Protein, *Acc Chem Res.* (Feb. 2004), 37(2):79-85.

(Continued)

*Primary Examiner* — Rita Desai
*Assistant Examiner* — Ben S Michelson
(74) *Attorney, Agent, or Firm* — Pepper Hamilton LLP

(57) ABSTRACT

Compounds that selectively bind to copper ions in a sample and methods of preparing and using the compounds are described. Disclosed herein are planar julolidine based compounds that display characteristic absorbance in the visible and near-infrared (NIR, 700-1000 nm) region in the presence of copper ions. Methods to detect $Cu^{2+}$ ions by fluorometry and colorimetry are disclosed.

6 Claims, 3 Drawing Sheets

(56) References Cited

OTHER PUBLICATIONS

O'Halloran et al., Mettalochaperones, an Intracellular Shuttle Service for Metal Ions, *The Journal of Biological Chemistry* (Aug. 18, 2000), 275(33):25057-25060.

Prodi et al., Luminescent chemosensors for transition metal ions, *Coordination Chemistry Review* (Dec. 31, 1999), 205:59-83.

Puig et al., Molecular mechanisms of copper uptake and distribution, *Chemical Biology* (2002), 6:171-180; *Berkeley Department of Education* http://nature.berkeley.edu/departments/nut/undergrad_glass/nst-160/Puig.pdf.

Rolinski et al., Near-infrared sensor for detecting copper ions in solution, *Advances in Fluorescence Sensing Technology III* (Feb. 9, 1997) (Abstract).

Rosenzweig et al., Structure and chemistry of the copper chaperone proteins, *Curr Opin Chem Biol.* (Apr. 2000), 4(2):140-147.

Shao et al., Copper Ion-Selective Fluorescent Sensor Based on the Inner Filter Effect Using a Spiropyran Derivative, *Analytical Chemistry* (Oct. 13, 2005), 77(22):7294-7303 (Abstract).

Singh et al., Combinatorial approach to the development of fluorescent sensors for nanomolar aqueous copper, *Tetrahedron Letters* (Sep. 28, 2000), 41:9601-9605.

Shnek et al., Metal-Induced Dispersion of Lipid Aggregates: A Simple, Selective, and Sensitive Fluorescent Metal Ion Sensor, *Angewandte Chemie International Edition in English* (Dec. 22, 2003), 34(8):905-907 (Abstract).

Swamy et al., Boronic acid-linked fluorescent and colorimetric probes for copper ions, *Chemical Communications* (Oct. 14, 2008), 45:5915-5917 (Abstract).

Torrado et al., Exploiting Polypeptide Motifs for the Design of Selective Cu(II) Ion Chemosensors, *J. Am. Chem. Soc.* (Jan. 7, 1998), 120(3):609-610 (Abstract).

Uauy et al., Essentiality of copper in humans, *Am J Clin Nutr* (1998), 67:952S-959S.

Valentine et al., Misfolded CuZnSOD and amyotrophic lateral sclerosis, *PNAS* (Apr. 1, 2003), 100(7):3617-3622.

Valeur et al., Design principles of fluorescent molecular sensors for cation recognition, *Coordination Chemistry Reviews* (Dec. 31, 1999), 205:3-40.

Vulpe et al., Isolation of a candidate gene for Menkes disease and evidence that it encodes a copper-transporting ATPase, *Nature Genetics* (1993), 3:7-13.

Waggoner et al., The role of copper in neurodegenerative diseases, *Neurobiology of Disease* (1999), 6(4):221-230 (Abstract).

\* cited by examiner

JULOLIDINE CONJUGATES AND METHODS FOR THEIR PREPARATION AND USE

BACKGROUND

Molecular sensors have been developed for selective recognition of different species on the basis of host-guest interactions making use of hydrogen bonding, electrostatic force, metal-ligand coordination, and hydrophobic and van der Waals interactions. In recent years, the development of colorimetric and fluorescent sensors of biologically active metal ions has been actively investigated because of their potential applications in life sciences, medicine, chemistry, and biotechnology. The design and synthesis of highly selective sensors for metal ions, such as mercury, lead, iron, zinc, and copper is particularly important, since these metal ions can have detrimental effects on the environment and human health.

Copper is one of the relatively small group of trace metal nutrients that are essential to sustain normal human health. The adult human body contains between 1.4-2.1 mg of copper per kilogram of body weight under normal conditions. Copper-dependent enzymes are involved in a number of physiological functions such as providing energy for biochemical reactions, transforming melanin for skin pigmentation, assisting in formation of cross-links in collagen and elastin, and thereby maintaining and repairing connective tissues. Copper in excessive amounts can be toxic and may cause oxidative stress and disorders associated with neurodegenerative diseases including Alzheimer's, Parkinson's, Menkes, Wilson's, and prion diseases. Although protein and organically bound copper appears to be less toxic, free solvated $Cu^{2+}$ may be particularly damaging since it catalyzes the formation of reactive organic species (ROS), including radical and non-radical species, which can trigger oxidative damage to proteins, nucleic acids, and lipids. The common nutritional deficiencies of zinc, manganese, and other trace minerals also facilitate the accumulation of very high levels of copper.

Many colorimetric and fluorescent chemosensors have been reported for sensing metal ions, with absorbance and emission in the visible region. However, the visible region spectrum suffers from various drawbacks such as lack of penetration into the test sample due to absorption and scattering of light. Further, the presence of autofluorescence generated from the chromophores and macromolecules present in the analytic samples impede the use of fluorescent chemosensors. These limitations can be overcome by the use of NIR radiation as they can penetrate the sample much deeper due to limited absorption and scattering. Therefore, there exists a need to develop molecular probes with NIR (700-1000 nm) optical responses for detecting metal ions.

SUMMARY

This disclosure is not limited to the particular systems, devices and methods described, as these may vary. The terminology used in the description is for the purpose of describing the particular versions or embodiments only, and is not intended to limit the scope.

In one embodiment, a class of bi-julolidine compounds for selective detection of copper ions and methods of their preparation are provided. In one embodiment, the bi-julolidine compound is of the following structure:

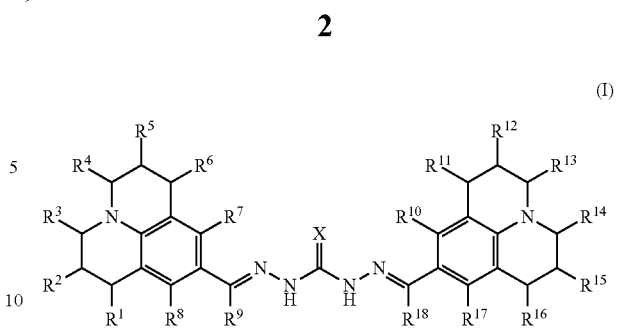

(I)

wherein X is an oxygen atom or a sulfur atom, and wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$ and $R^{18}$ are independently selected from the group consisting of hydrogen, halogen, hydroxyl, alkyl, substituted alkyl, alkoxy, substituted alkoxy, aryl, substituted aryl, heteroaryl, substituted heteroaryl, amino, substituted amino, alkylamino, substituted alkylamino, azido, nitro, nitroso, cyano, thioether, aldehyde, carboxyl, sulfoalkyl, carboxyalkyl and amino alkyl.

In another embodiment, a method for synthesizing a bi-julolidine compound may include contacting a julolidine compound with a carbohydrazide or a thiocarbohydrazide to form a reaction mixture, heating the reaction mixture, cooling the reaction mixture and collecting the precipitate. The julolidine compound is represented by the structure:

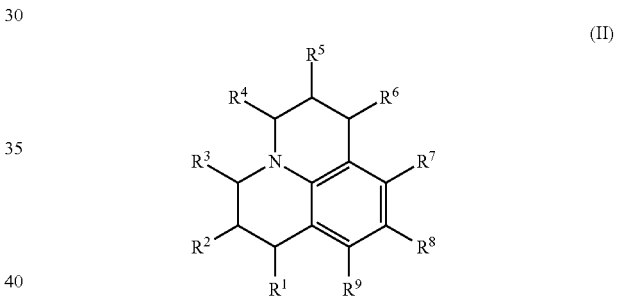

(II)

wherein $R^1$, $R^2$, $R^3$, $R^4$, $R^5$, $R^6$, $R^7$, $R^8$ and $R^9$ are independently selected from the group consisting of hydrogen, halogen, hydroxyl, alkyl, substituted alkyl, alkoxy, substituted alkoxy, aryl, substituted aryl, heteroaryl, substituted heteroaryl, amino, substituted amino, alkylamino, substituted alkylamino, azido, nitro, nitroso, cyano, thioether, aldehyde, carboxyl, sulfoalkyl, carboxyalkyl and amino alkyl.

In an additional embodiment, a method for selectively detecting copper ions in a sample may include contacting a bi-julolidine compound with the sample for a sufficient time to allow the formation of a complex between any copper ions and the compound, wherein the compound has the structure:

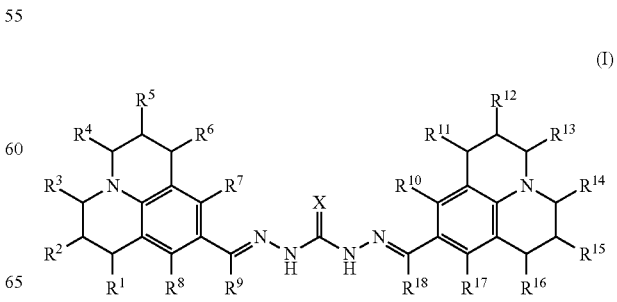

(I)

wherein X is an oxygen atom or a sulfur atom, and wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}R^{16}$, $R^{17}$ and $R^{18}$ are independently selected from the group consisting of hydrogen, halogen, hydroxyl, alkyl, substituted alkyl, alkoxy, substituted alkoxy, aryl, substituted aryl, heteroaryl, substituted heteroaryl, amino, substituted amino, alkylamino, substituted alkylamino, azido, nitro, nitroso, cyano, thioether, aldehyde, carboxyl, sulfoalkyl, carboxyalkyl and amino alkyl. The method further includes comparing a visual color, absorption spectra or fluorescence emission spectra of the julolidine compound in the presence of the sample to the visual color, absorption spectra or fluorescence emission spectra of the compound in the absence of the sample, wherein a difference in the visual color, the absorption spectra or the fluorescence emission spectra of the compound in the presence of the sample as compared to the absence of the sample indicates the presence of copper ions in the sample.

In a further embodiment, kits for detection and quantification of copper ions are provided. For example, a kit is provided for measuring the concentration of copper ions in a sample that includes a julolidine compound, as described herein. The kit can further include one or more additional components, such as a standard solution of copper ions, a buffer, a positive control, a negative control, and written instructions for detecting copper ions in a sample using colorimetry, absorption spectroscopy or fluorescence spectroscopy.

DETAILED DESCRIPTION

Figure 1:
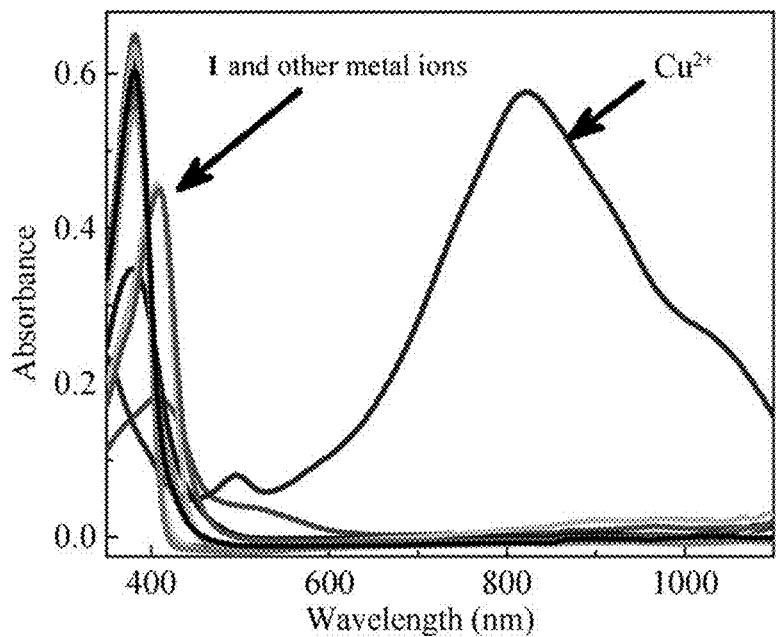
FIG. 1 depicts the UV/Vis absorption spectra of compound 1 (10.0 μM) in the presence and absence of addition of salts (50.0 equiv.) of $Li^+$, $Na^+$, $Ba^{2+}$, $Sr^{2+}$, $Mg^{2+}$, $Al^{3+}$, $Ca^{2+}$, $Mn^{2+}$, $Fe^{2+}$, $Co^{2+}$, $Ni^{2+}$, $Zn^{2+}$, $Ag^+$, $Cd^{2+}$, $Hg^{2+}$, $Pb^{2+}$ and $Cu^{2+}$ in aqueous medium (50 mM HEPES/$CH_3CN$, 6:4, v/v; pH 7.2).

Compounds that selectively bind to copper ions in a sample and methods to detect copper ions are described. Planar julolidine based ligands that can detect $Cu^{2+}$ by colorimetric and fluorometric methods, with additional characteristic absorbance in the near-infrared (NIR, 700-1000 nm) region are provided.

Unless defined otherwise, all technical and scientific terms used herein have the same meaning as commonly understood by one of ordinary skill in the art to which this disclosure is related. The following terms are defined for purposes of the disclosure as described herein:

"Alkyl" refers to monovalent saturated aliphatic hydrocarbyl groups having from 1 to 20 carbon atoms and preferably 1 to 10 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3$)$_2$CH—), n-butyl ($CH_3CH_2CH_2CH_2$—), isobutyl (($CH_3$)$_2$CHCH$_2$—), sec-butyl (($CH_3$)($CH_3CH_2$)CH—) and t-butyl (($CH_3$)$_3$C—).

"Alkoxy" refers to the group —O-alkyl wherein alkyl is defined herein. Alkoxy includes, by way of example, methoxy, ethoxy, n-propoxy, isopropoxy, n-butoxy, t-butoxy, sec-butoxy, and n-pentoxy.

"Aryl" refers to a aromatic carbocyclic group of from 5 to 14 carbon atoms having a single ring (e.g., benzo) or multiple condensed rings (e.g., naphthyl or anthryl) which condensed rings may or may not be aromatic.

"Halogen" refers to fluoro, chloro, bromo and iodo.

"Heteroaryl" refers to an aromatic group that contains at least one heteroatom selected from the group consisting of oxygen, nitrogen and sulfur within the ring. Such heteroaryl groups can have a single ring (e.g., pyridinyl or furyl) or multiple condensed rings (e.g., indolizinyl or benzothienyl) wherein the condensed rings may or may not be aromatic and/or contain a heteroatom.

"Near-infrared" (NIR) radiation refers to a radiation having a wavelength of about 700 nm to about 1100 nm.

In one embodiment, bi-julolidine compounds are provided having a formula:

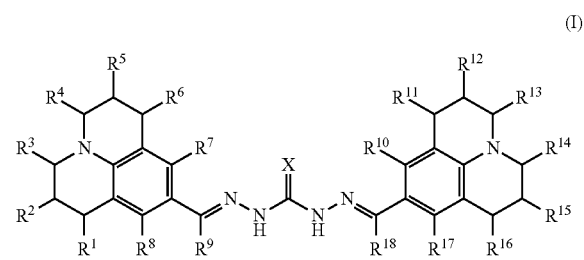

(I)

wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$ and $R^{18}$ are independently selected from the group consisting of hydrogen, halogen, hydroxyl, alkyl, substituted alkyl, alkoxy, substituted alkoxy, aryl, substituted aryl, hetero aryl, substituted heteroaryl, amino, substituted amino, alkylamino, substituted alkylamino, azido, nitro, nitroso, cyano, thioether, aldehyde, carboxyl, sulfoalkyl, carboxyalkyl and amino alkyl. Substituent X in the above formula may be an oxygen atom or a sulfur atom. Specific examples of the compound include a julolidine-carbonohydrazone (compound 1) and a julolidine-thiocarbonohydrazone (compound 2), as shown below.

compound 1

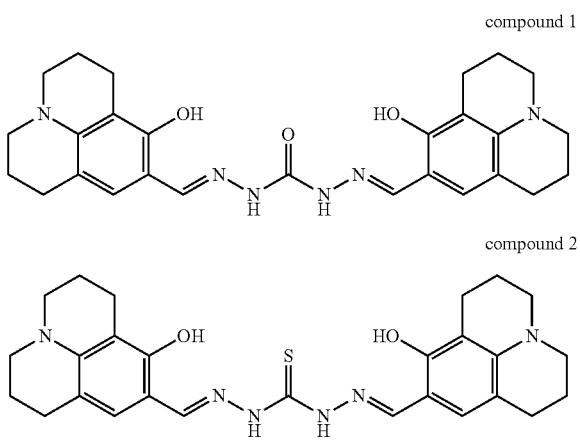

compound 2

Compounds may also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Examples of prototropic tautomers include, but are not limited to, alkylene acylhydrazide-acyl alkyldiazene pairs,

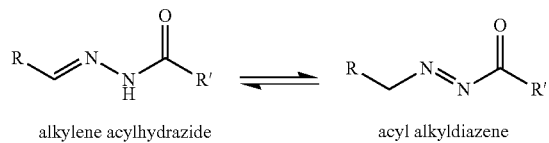

alkylene acylhydrazide      acyl alkyldiazene alkylene acylhydrazide acyl alkyldiazene ketone-enol pairs, amide-imidic acid pairs, lactam-lactim pairs, amide-imidic acid pairs, enamine-imine pairs, and annular forms where a proton can occupy two or more positions of a heterocyclic system including, but not limited to, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Many geometric isomers of olefins, C=N double bonds, and the like can also be present in the compounds described herein, and all such stable isomers are contemplated in the present invention. Cis and trans geometric isomers of the compounds are also included within the scope of the invention and can be isolated as a mixture of isomers or as separated isomeric forms. Where a compound capable of stereoisomerism or geometric isomerism is designated in its structure or name without reference to specific R/S or cis/trans configurations, it is intended that all such isomers are contemplated.

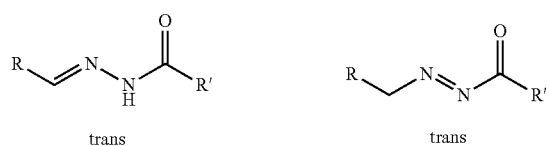

trans      trans

-continued

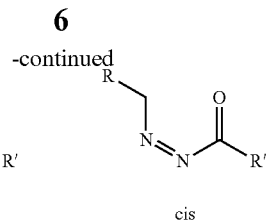

cis      cis

The compounds have selective affinity for $Cu^{2+}$ ions. The typical association constants (log $K_a$) of the compounds for $Cu^{2+}$ are in the range of about $1 M^{-1}s^{-1}$ to about $50 M^{-1}s^{-1}$, or about $10 M^{-1}s^{-1}$ to about $50 M^{-1}s^{1}$, or about $1 M^{-1}s^{-1}$ to about $40 M^{-1}s^{-1}$, or about $10 M^{-1}s^{-1}$ to about $40 M^{-1}s^{-1}$. Specific examples of association constant include about $10 M^{-}s^{-1}$, about $12 M^{-}s^{-1}$, about $13.52 M^{-}s^{-1}$, about $14.36 M^{-}s^{-1}$, about $15 M^{-1}s^{-1}$, and ranges between any two of these values. In one embodiment, the compound selectively binds to $Cu^{2+}$ ions and does not bind substantially to other metal ions such as $Li^+$, $Na^+$, $Ba^{2+}$, $Sr^{2+}$, $Mg^{2+}$, $Al^{3+}$, $Ca^{2+}$, $Mn^{2+}$, $Fe^{2+}$, $Co^{2+}$, $Ni^{2+}$, $Zn^{2+}$, $Ag^+$, $Cd^{2+}$, $Hg^{2+}$, or $Pb^{2+}$. In one embodiment, the compound selectively binds to $Cu^{2+}$ even in the presence of excess of other metal ions.

In some embodiments, the bi-julolidine compounds have characteristic absorption spectra in the range of about 350 nm to about 400 nm in the absence of $Cu^{2+}$ ions. However, they exhibit different absorption spectra in the presence of $Cu^{2+}$ ions. Upon contacting $Cu^{2+}$ ions, these compounds exhibit NIR spectra in the range of about 700 nm to about 1100 nm, or about 700 nm to about 1000 nm, or about 800 nm to about 1100 nm. Specific examples of the absorption spectra in the NIR range include about 820 nm, about 823 nm, about 930 nm, about 980 nm, and ranges between any two of these values. Further, these compounds do not significantly display NIR spectra in the presence of other ions such as $Li^+$, $Na^+$, $Ba^{2+}$, $Sr^{2+}$, $Mg^+$, $Al^{3+}$, $Ca^{2+}$, $Mn^{2+}$, $Fe^{2+}$, $Co^{2+}$, $Ni^{2+}$, $Zn^{2+}$, $Ag^+$, $Cd^{2+}$, $Hg^{2+}$, or $Pb^{2+}$. This is explained in reference to FIG. 1 and FIG. 2 in detail.

In other embodiments, the bi-julolidine compounds also exhibit absorption spectra in the visible range upon contacting $Cu^{2+}$, in the range of about 460 nm to about 600 nm, or about 460 nm to about 550 nm, or about 460 nm to about 500 nm. Specific examples of the absorption spectra in the visible range include about 495 nm, about 500 nm, about 525 nm, about 570 nm, and ranges between any two of these values. Further, these compounds do not significantly display visible spectra in the presence of other ions such as $Li^+$, $Na^+$, $Ba^{2+}$, $Sr^{2+}$, $Mg^{2+}$, $Al^{3+}$, $Ca^{2+}$, $Mn^{2+}$, $Fe^{2+}$, $Co^{2+}$, $Ni^{2+}$, $Zn^{2+}$, $Ag^+$, $Cd^{2+}$, $Hg^{2+}$, or $Pb^{2+}$. This is explained in detail in reference to FIG. 1 and FIG. 2.

In some embodiments, the compounds also exhibit quenching of fluorescence in the presence of $Cu^{2+}$ ions. For example, compound 2 shows strong fluorescence emission at about 535 nm upon excitation at about 430 nm. The fluorescence intensity at about 535 nm is quenched in the presence of only $Cu^{2+}$ with about 430 nm excitation, whereas no significant changes were observed in the fluorescence emission of compound 2 in the presence of other metal ions such as $Li^+$, $Na^+$, $Ba^{2+}$, $Sr^{2+}$, $Mg^{2+}$, $Al^{3+}$, $Ca^{2+}$, $Mn^{2+}$, $Fe^{2+}$, $Co^{2+}$, $Ni^{2+}$, $Zn^{2+}$, $Ag^+$, $Cd^{2+}$, $Hg^{2+}$, or $Pb^{2+}$, under similar conditions. This is explained in detail in reference to FIG. 5A.

In some embodiments, the bi-julolidine compounds display visible and NIR range absorbance in the presence of $Cu^{2+}$ ions over a wide range of pH. Specific pH ranges include, but not limited to, from about pH 2 to about pH 11, from about pH 2 to about pH 10, from about pH 2 to about pH 9. Specific examples of the pH value include pH 6, pH 7, pH 7.2, pH 8, and ranges between any two of these values.

Also provided herein are methods to prepare the bi-julolidine compounds. In some embodiments, a method for synthesizing a bi-julolidine compound may include reacting a julolidine compound with a carbohydrazide or a thiocarbohydrazide under a reflux, cooling the reaction mixture and collecting the precipitate. The julolidine compound is represented by the formula:

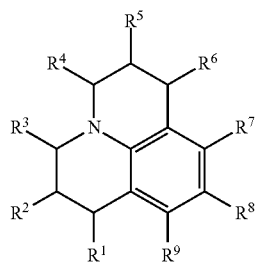

wherein $R^1$, $R^2$, $R^3$, $R^4$, $R^5$, $R^6$, $R^7$, $R^8$ and $R^9$ are independently selected from the group consisting of hydrogen, halogen, hydroxyl, alkyl, substituted alkyl, alkoxy, substituted alkoxy, aryl, substituted aryl, heteroaryl, substituted heteroaryl, amino, substituted amino, alkylamino, substituted alkylamino, azido, nitro, nitroso, cyano, thioether, aldehyde, carboxyl, sulfoalkyl, carboxyalkyl and amino alkyl. Specific time periods for reflux reaction may include about 8 hours, about 10 hours, about 12 hours, about 16 hours, about 20 hours, about 22 hours, about 24 hours, about 26 hours, about 30 hours, or about 36 hours. Specific temperatures at which the reaction mixture is cooled may include, about 10° C., about 15° C., about 20° C., about 25° C., or about 30° C.

In some embodiments, methods for selectively detecting copper ions in a sample are provided. In some embodiments, a method may include contacting the bi-julolidine compound with the sample for a sufficient time to allow the formation of a complex between any copper ions and the compound, wherein the compound has the formula:

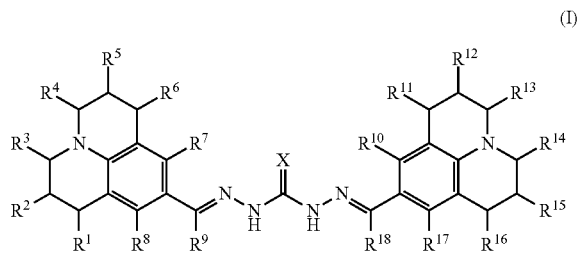

wherein X is an oxygen atom or a sulfur atom, and wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}R^{16}$, $R^{17}$ and $R^{18}$ are independently selected from the group consisting of hydrogen, halogen, hydroxyl, alkyl, substituted alkyl, alkoxy, substituted alkoxy, aryl, substituted aryl, heteroaryl, substituted heteroaryl, amino, substituted amino, alkylamino, substituted alkylamino, azido, nitro, nitroso, cyano, thioether, aldehyde, carboxyl, sulfoalkyl, carboxyalkyl and amino alkyl. The method further includes comparing a visual color, absorption spectra or fluorescence emission spectra of the bi-julolidine compound in the presence of the sample to the visual color, absorption spectra or fluorescence emission spectra of the compound in the absence of the sample, wherein a difference in the visual color, the absorption spectra or the fluorescence emission spectra of the compound in the presence of the sample as compared to the absence of the sample indicates the presence of copper ions in the sample.

In various embodiments, the methods disclosed herein can be used to determine the concentration of copper ions in a sample. The change in the visible and NIR absorption spectra of the bi-julolidine compound can be correlated to the concentration of copper ions. Thus, a comparison of the absorption or fluorescence spectra of the compound in the presence of unknown concentration of $Cu^{2+}$ ions to a standard curve of the absorption or fluorescence spectra of the compound in the presence of known concentrations of $Cu^{2+}$ can provide the concentration of the $Cu^{2+}$ ions in the sample.

In some embodiments, the bi-julolidine compounds can be used to detect copper ions based on visual color change. For example, a solution of compound 1 is colorless in the absence of $Cu^{2+}$ ions. In the presence of increasing concentration of $Cu^{2+}$ ions, a solution of compound 1 turns to light green, then to light purple, and then to aqua color. Similarly, a solution of compound 2 changes color in the presence of increasing concentrations of $Cu^{2+}$ from light green to light violet, then to light blue and then to greenish aqua. Thus, a comparison of the color of compound solution in the presence of a sample containing $Cu^{2+}$ ions to the color of the compound solution in the presence of known amount of $Cu^{2+}$ ions will provide the concentration of the $Cu^{2+}$ ions in the sample.

In some embodiments, the bi-julolidine compounds can be used to detect the concentration of $Cu^{2+}$ ions in a sample, the concentrations being in the range of about 1 µM to about 1 M, about 5 µM to about 1M, about 70 µM to about 1 M, about 100 µM to about 1 M, about 500 µM to about 1 M. Specific examples of the concentrations of $Cu^{2+}$ ions can include 1 µM, 2 µM, 5 µM, 10 µM, 20 µM, 30 µM, 40 µM, 50 µM, and ranges between any two of these values.

In some embodiments, methods are provided for detecting the presence of copper ions by fluorometry. Such methods include detecting the fluorescence of the bi-julolidine compound in the presence of the sample containing $Cu^{2+}$ ions and comparing the detected fluorescence to that of the fluorescence of the bi-julolidine compound in the absence of the sample, wherein a reduction in fluorescence of the compound in the presence of the sample as compared to the absence of the sample indicates the presence of copper ions in the sample.

In some embodiments, methods are provided to detect $Cu^{2+}$ ions in biological systems such as living cells. For example, the bi-julolidine compounds are added in the growth media of adherent eukaryotic cells for a brief period (about 10 minutes) and the excess of the compound is washed off by rinsing the cells with phosphate-buffered saline. The cells are placed under a fluorescent microscope and a fluorescence emission of the compound is observed at a wavelength between 450 nm and 650 nm after excitation with a wavelength of about 400 nm to about 430 nm. The compounds are cell-permeable and can detect the presence of $Cu^{2+}$ ions in different compartments of the cell.

In some embodiments, the optical response of the bi-julolidine compounds can be detected by using any of the following devices, without limitation, CCD cameras, video cameras, photographic film, laser-scanning devices, fluorometers, photodiodes, quantum counters, epifluorescence microscopes, scanning microscopes, flow cytometers, fluorescence microplate readers, spectrophotometers and colorimeters. The optical response of the bi-julolidine compounds may also be detected by visual inspection.

Compounds disclosed herein are useful for detecting $Cu^{2+}$ ions in a sample. In some embodiments, samples include, but not limited to, inorganic solutions, organic solutions, cellular components, proteins, peptides, buffer solutions, intracellular fluids, extracellular fluids, biological fermentation media, environmental sample, industrial samples, living cells, tissues, blood, urine, saliva, eukaryotic cells, prokaryotic cells, water, waste water, sea water, foodstuffs, beverages, or combinations thereof.

In some embodiments, the compounds are incorporated into kits that facilitate the detection of copper ions. The kits can be packaged with the compound in a dry form or with the compound in solution. The kit can further include one or more additional components, such as a standard solution of copper ions, a buffer, a positive control, a negative control, and written instructions for detecting copper ions in a sample using colorimetry, absorption spectroscopy or fluorescence spectroscopy.

EXAMPLES

Example 1

Synthesis of Compound 1 and Compound 2

A solution of 8-hydroxyjulolidinal (6 mmoles) in ethanol (40 mL) was added slowly over a period of 30-90 minutes to a solution of carbohydrazide (3 mmoles) or thiocarbohydrazide (3 mmoles) in water (40 mL). The reaction mixture was heated to reflux for 24 hours with constant stiffing. The reaction mixture was cooled to room temperature and the precipitate was filtered. The precipitate was washed with ethanol and dried under vacuum to obtain bi-julolidine compounds julolidine-carbonohydrazone (compound 1) and julolidine-thiocarbonohydrazone (compound 2), respectively.

Example 2

UV/Visible Absorption Spectra of Bi-Julolidine Compounds

The photophysical properties of bi-julolidine compounds were investigated by monitoring the absorption spectral behavior upon addition of several metal ions such as $Li^+$, $Na^+$, $Ba^{2+}$, $Sr^{2+}$, $Mg^{2+}$, $Al^{3+}$, $Ca^{2+}$, $Mn^{2+}$, $Fe^{2+}$, $Co^{2+}$, $Ni^{2+}$, $Zn^{2+}$, $Ag^+$, $Cd^{2+}$, $Hg^{2+}$, $Pb^{2+}$ and $Cu^{2+}$ in an aqueous buffer medium (50 mM, 2-(4-(2-hydroxyethyl)-1-piperazin-yl)ethanesulfonic acid (HEPES)/$CH_3CN$, 6:4, v/v; pH 7.2). Bi-julolidine compounds showed an absorption band centered around 380 nm, which remained unchanged upon addition of 50.0 equivalents of metal ions $Li^+$, $Na^+$, $Ba^{2+}$, $Sr^{2+}$, $Mg^{2+}$, $Al^{3+}$, $Ca^{2+}$, $Mn^{2+}$, $Fe^{2+}$, $Ag^+$, $Cd^{2+}$, $Pb^{2+}$. With the addition of 50.0 equivalents of $Co^{2+}$, $Ni^{2+}$and $Zn^{2+}$, the absorbance intensity decreased and slightly red shifted to different extents ($Ni^{2+}$=408.5 nm; $Zn^{2+}$=410 nm; $Co^{2+}$=409 nm).

Figure 2:
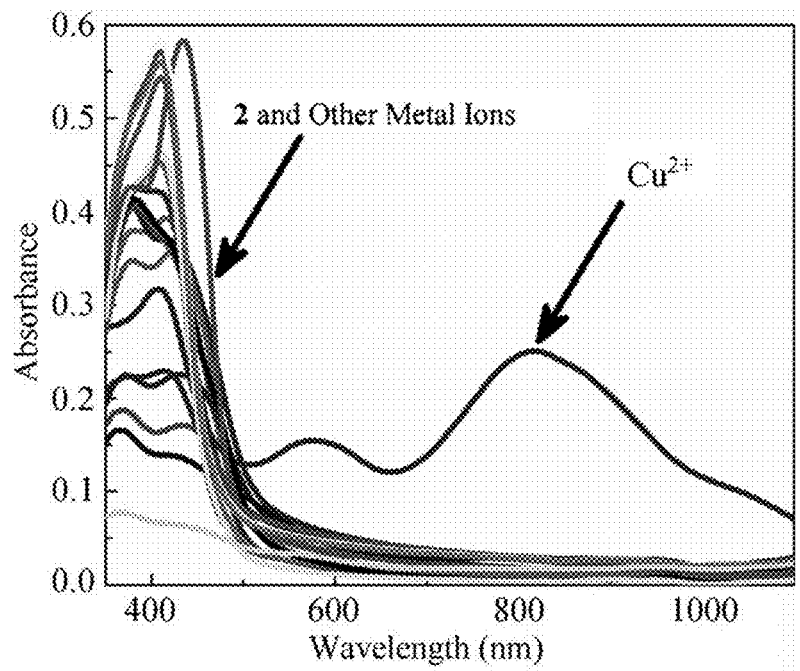
FIG. 2 depicts the UV/Vis absorption spectra of compound 2 (10.0 μM) in the presence and absence of addition of salts (50.0 equiv.) of $Li^+$, $Na^+$, $Ba^{2+}$, $Sr^{2+}$, $Mg^{2+}$, $Mg^{3+}$, $Ca^{2+}$, $Mn^{2+}$, $Fe^{2+}$, $Co^{2+}$, $Ni^{2+}$, $Zn^{2+}$, $Ag^+$, $Cd^{2+}$, $Hg^{2+}$, $Pb^{2+}$ and $Cu^{2+}$ in aqueous medium (50 mM HEPES/$CH_3CN$, 6:4, v/v; pH 7.2).

At a similar concentration of $Cu^{2+}$ (50.0 equiv), julolidine-carbonohydrazone compound showed characteristic absorbance in the visible (495 nm) and NIR (823 nm) regions. Similarly, julolidine-thiocarbonohydrazone compound exhibited an absorption band in the visible region (570 nm) accompanied by a well-distinguished NIR absorption band around 820 nm. Representative examples are shown in FIG. 1 and FIG. 2 using compound 1 and 2, respectively.

Example 3

Figure 3:
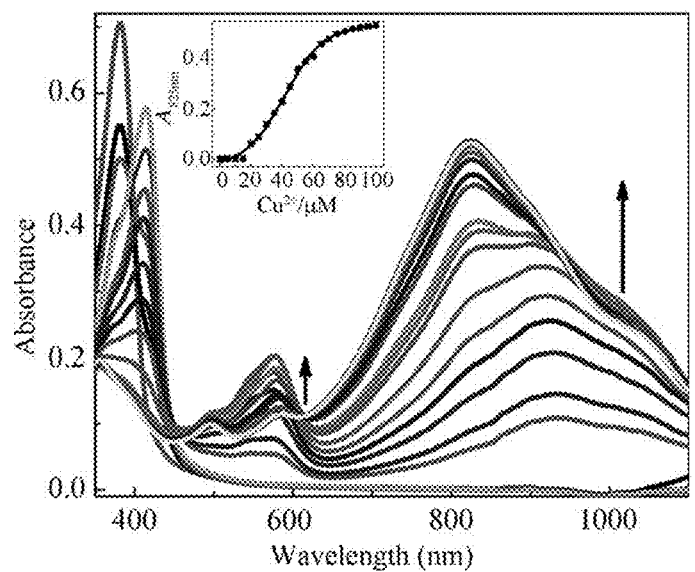
FIG. 3 depicts the UV/Vis absorption spectra of compound 1 (10.0 μM) on addition of different concentrations of $Cu^{2+}$ (0, 2.5, 5, 10, 15, 20, 25, 30, 35, 40, 45, 50, 55, 60, 65, 70, 75, 80, 85, 90, 95, and 100 μM) in aqueous medium (50 mM HEPES/$CH_3CN$, 6:4, v/v; pH 7.2). Inset: Absorbance at 825 nm as a function of $Cu^{2+}$.

UV/Visible Absorption Spectra and Colorimetric Properties of Bi-Julolidine Compounds with Increasing Concentrations of $Cu^{2+}$ Ions The spectral and colorimetric properties of bi-julolidine compounds were investigated by monitoring the absorption spectral behavior upon addition of increasing concentrations of $Cu^{2+}$ in an aqueous buffer medium (50 mM, 2-(4-(2-hydroxyethyl)-1-piperazin-yl)ethanesulfonic acid (HEPES)/$CH_3CN$, 6:4, v/v; pH 7.2). During sequential titration, the absorption spectra of julolidine-carbonohydrazone compound in the visible region gradually shifted from 380 nm to 412 nm with the addition of 1.5 equivalents of $Cu^{2+}$ and the colorless solution turned to light green. Increasing the concentration of $Cu^{2+}$ in the solution of julolidine-carbonohydrazone compound from 1.5 to 2.0 equivalents led to a change in the solution color from light green to light purple. A new absorption band ($\lambda_{max}$=570 nm) appeared in the visible region accompanied by a distinguishable NIR band with $\lambda_{max}$ centered at 930 nm. The absorbance at 570 nm reached a maximum upon addition of 6.0 equivalents of $Cu^{2+}$ with an extinction coefficient ($\epsilon$) of $2 \times 10^4$ $M^{-1}cm^{-1}$ and then decreased with further addition of $Cu^{2+}$. The absorbance in the NIR region reached a maximum ($\epsilon$=$5.2 \times 10^4$ $M^{-1}cm^{-1}$) upon addition of a total of 8.0 equivalents of $Cu^{2+}$ with a gradual shift of $\lambda_{max}$ from 930 nm to 825 nm, and that remained unchanged upon further addition of $Cu^{2+}$. The final solution color of julolidine-carbonohydrazone compound was aqua colored. A representative colorimetric titration of compound 1 with sequential addition of $Cu^{2+}$ is shown in FIG. 3.

Figure 4:
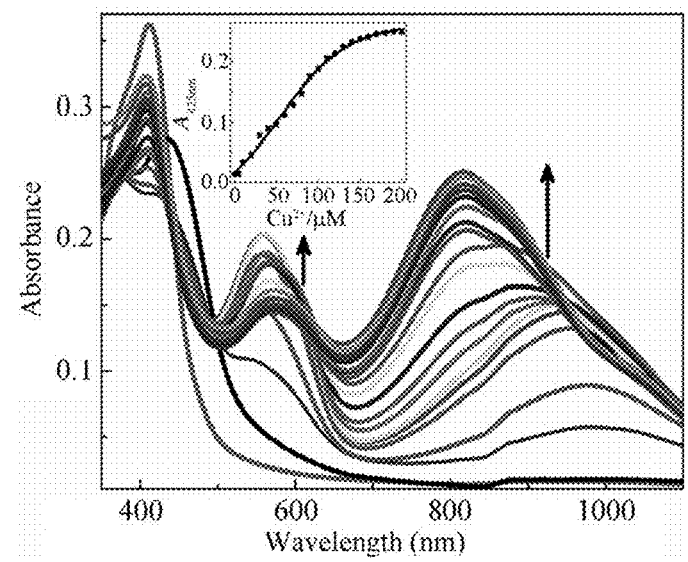
FIG. 4 depicts the UV/Vis absorption spectra of compound 2 (10.0 μM) on addition of different concentrations of $Cu^{2+}$ (0, 5, 10, 20, 30, 40, 50, 60, 70, 80, 90, 100, 110, 120, 130, 140, 150, 160, 170, 180, 190, and 200 μM) in aqueous medium (50 mM HEPES/$CH_3CN$, 6:4, v/v; pH 7.2). Inset: Absorbance at 825 nm as a function of $Cu^{2+}$.

During sequential titration of $Cu^{2+}$ with julolidine-thiocarbonohydrazone compound, two absorption bands appeared at 570 nm and 980 nm, after addition of 1.0 equivalent of $Cu^{2+}$. At that concentration of $Cu^{2+}$ ions, the color of the solution of julolidine-thiocarbonohydrazone compound changed from greenish to light purple. The absorbance at 570 nm and 980 nm were enhanced when $Cu^{2+}$ concentrations increased from 1.5 to 2.0 equivalents and the purple-colored solution turned to light violet. The absorbance at 570 nm reached a maximum at 5.0 equivalents of $Cu^{2+}$ with an extinction coefficient ($\epsilon$) of $2 \times 10^4 M^{-1}$ $cm^{-1}$ and a consequent increase in the intensity of the NIR absorption band was observed. At that concentration of $Cu^{2+}$ ions, The solution color of julolidine-thiocarbonohydrazone compound changed from light violet to blue. Further addition of $Cu^{2+}$ resulted in a gradual decrease in the absorbance at 570 nm, but the absorbance in the NIR region increased to 820 nm and reached a maximum (E=$5.2 \times 10^4$ $M^{-1}cm^{-1}$) upon addition of 15.0 equivalents of $Cu^{2+}$. The final solution color of julolidine-thiocarbonohydrazone compound was greenish aqua. A representative colorimetric titration of compound 2 with sequential addition of $Cu^{2+}$ is shown in FIG. 4.

Example 4

Fluorometric Detection of Copper Ions Using Julolidine-Thiocarbono Hydrazone

Figure 5A:
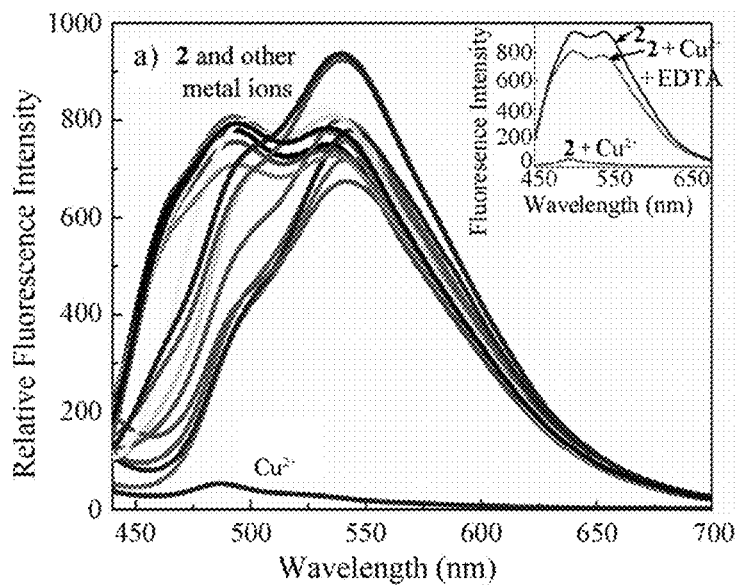
FIG. 5A depicts the fluorescence spectra of compound 2 (10.0 μM) in the presence and absence of addition of salts (20.0 equiv.) of $Li^+$, $Na^+$, $Ba^{2+}$, $Sr^{2+}$, $Mg^+$, $Al^{3+}$, $Ca^{2+}$, $Mn^{2+}$, $Fe^{2+}$, $Co^{2+}$, $Ni^{2+}$, $Zn^{2+}$, $Ag^+$, $Cd^{2+}$, $Hg^{2+}$, $Pb^{2+}$ and $Cu^{2+}$ in aqueous medium (50 mM HEPES/$CH_3CN$, 6:4, v/v; pH 7.2). Inset: Fluorescence spectra of compound 2, compound 2+$Cu^{2+}$ and compound 2+$Cu^{2+}$+EDTA.
Figure 5B:
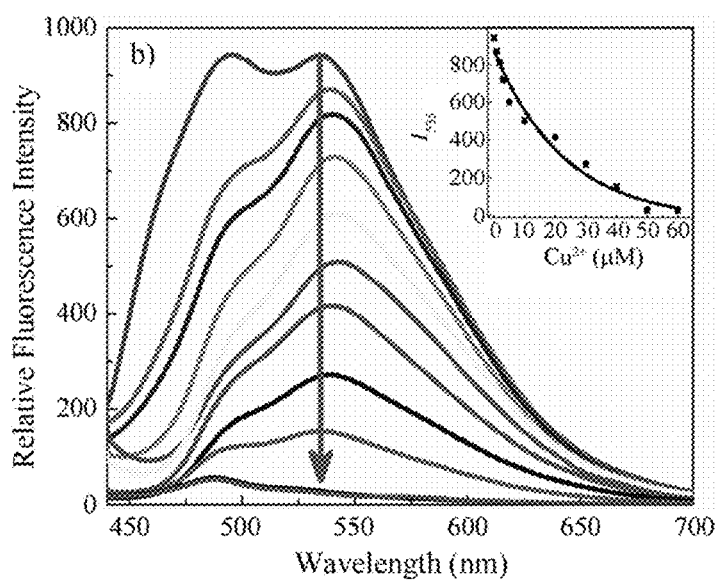
FIG. 5B depicts the fluorescence spectra of compound 2 (10.0 μM) on addition of different concentrations of $Cu^{2+}$ (0, 1, 2, 3, 5, 10, 20, 30, 40, 50, and 60 μM) in aqueous medium. Inset: Intensity at 535 nm as a function of $Cu^{2+}$.

The fluorometric behavior of julolidine-thiocarbonohydrazone compound was studied upon addition of 20.0 equivalents of $Li^+$, $Na^+$, $Ba^{2+}$, $Sr^{2+}$, $Mg^{2+}$, $Ag^+$, $Ca^{2+}$, $Mn^{2+}$, $Fe^{2+}$, $CO^{2+}$, $Ni^{2+}$, $Zn^{2+}$, $Ag^+$, $Cd^{2+}$, $Hg^{2+}$, $Pb^{2+}$ and $Cu^{2+}$ in an aqueous buffer medium (50 mM, 2-(4-(2-hydroxyethyl)-1-piperazin-yl)ethanesulfonic acid (HEPES)/$CH_3CN$, 6:4, v/v;

pH 7.2). Julolidine-thiocarbonohydrazone compound demonstrated a strong fluorescence emission around 535 nm upon excitation at 430 nm. The fluorescence intensity around 535 nm was quenched in the presence of only $Cu^{2+}$ ions, but not in the presence of other metal ions. The quenched fluorescence of julolidine-thiocarbonohydrazone compound was restored upon treating the julolidine-thiocarbonohydrazone compound —$Cu^{2+}$ complex with ethylenediaminetetraacetic acid (EDTA). A representative experiment using compound 2 is shown in FIG. 5A. Fluorescence emission of compound 2 with sequential addition of increasing concentrations (0 to 50 μM) of $Cu^{2+}$ is shown in FIG. 5B.

Example 5

Detection of $Cu^{2+}$ Ions in Cells Using Fluorescence Microscopy

HEK 293T cells were grown to 50% confluency in a 30 mm dish containing Dulbecco's modified eagle medium (DMEM) and 10% fetal bovine serum (FBS) at 37° C. and 5% $CO_2$. The cells were washed three times with phosphate-buffered saline (PBS) and stained with julolidine-thiocarbonohydrazone compound (10 μM final concentration) in the growth media without FBS for 10 minutes. The adherent cells were washed three times with PBS to remove excess compound. The cells were examined under fluorescence microscope with an excitation-emission wavelength of 450-650 nm, which demonstrated the presence of fluorescent julolidine-thiocarbonohydrazone compound in cells. To confirm these results, the cells were supplemented with Cu—$(ClO_4)_2.6H_2O$ (10 μM) in DMEM without FBS for 10 minutes. This resulted in complete suppression of intracellular fluorescence. Further, the excess of Cu—$(ClO_4)_2.6H_2O$ was washed off with PBS and then supplemented with EDTA (10 μM) in DMEM without FBS for 10 minutes. This resulted in the recovery of intracellular fluorescence. These studies demonstrated the cytoplasmic localization of julolidine-thiocarbonohydrazone compound and clearly suggested that the compound is cell-permeable and can respond to copper ions within living cells.

Example 6

Specificity of Bi-Julolidine Compounds Towards $Cu^{2+}$ Ions

The specificity of bi-julolidine Schiff-base compounds, compound 1 and compound 2, in detecting $Cu^{2+}$ ions were investigated by monitoring the absorption spectral behavior of the compounds. The experiment was also performed using other Schiff-base compounds that were prepared by condensing different salicylaldehyde derivatives with carbohydrazide and thiocarbohydrazide (compounds 3-8, shown below). Compounds 1 and 2 showed an absorption band centered around 380 nm in the absence of $Cu^{2+}$ ions, but showed a characteristic absorbance in the visible (495 nm for compound 1 and 570 nm for compound 2) and NIR (825 nm) regions in the presence of $Cu^{2+}$ ions. In contrast, the other Schiff-base ligands (compounds 3-8) failed to exhibit any characteristic optical response in the presence of $Cu^{2+}$ ions.

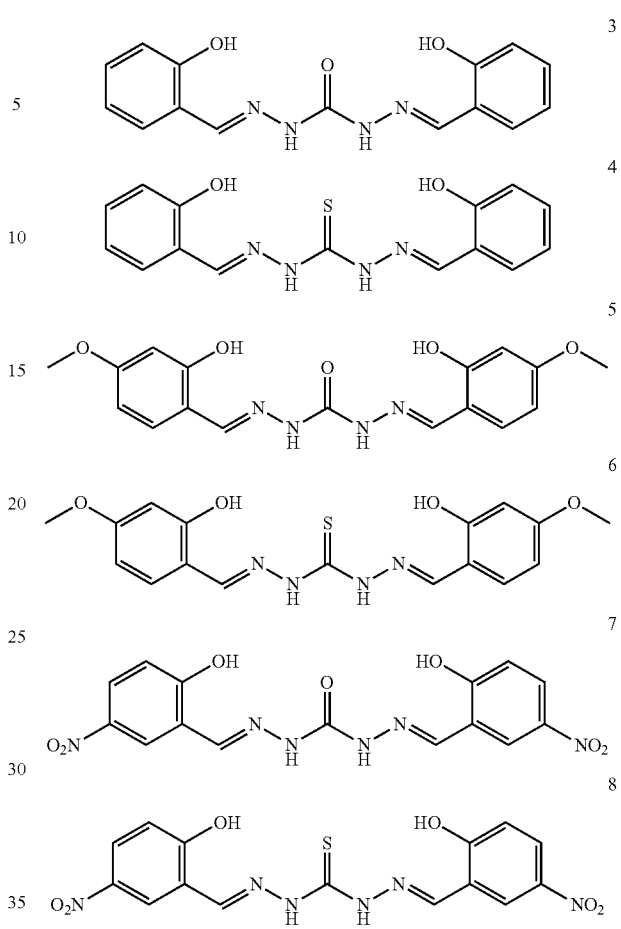

Example 7

Assay Kit to Measure Copper Ion Concentration

An assay kit to measure the concentration of copper ions in a sample (water) is demonstrated. The kit contains solutions of compound 1 and compound 2 in a buffer (50 mM, 2-(4-(2-hydroxyethyl)-1-piperazin-yl)ethanesulfonic acid (HEPES)/$CH_3CN$, 6:4, v/v; pH 7.2), and a solution of 100 mM copper sulfate. About 100 μl of test sample (water containing unknown concentration of copper ions) is mixed with 1 mL of compound 1 (or compound 2) solution, and the absorbance at 825 nm is read. Similarly, 100 μl of various concentrations of the copper sulfate solution (20 mM, 40 mM, 60 mM, 80 mM and 100 mM) is mixed with 1 mL of compound 1 (or compound 2) and their absorbance at 825 nm is read. A standard curve is plotted with these values and the amount of copper ions present in the test sample is determined using the standard curve.

This disclosure is not limited to the particular systems, devices and methods described, as these may vary. The terminology used in the description is for the purpose of describing the particular versions or embodiments only, and is not intended to limit the scope.

In the above detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

As used in this document, the singular forms "a", "an", and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior disclosure. As used in this document, the term "comprising" means "including, but not limited to."

While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

What is claimed is:

1. A bi-julolidine compound having the formula:

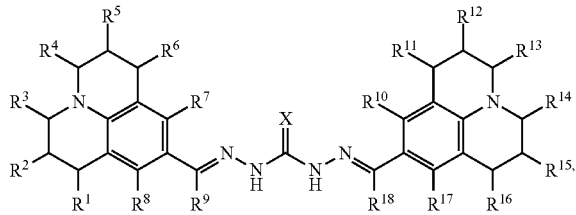

wherein X is an oxygen atom or a sulfur atom;
$R^1, R^2, R^3, R^4, R^5, R^6, R^8, R^9, R^{11}, R^{12}, R^{13}, R^{14}, R^{15}, R^{16}, R^{17}$ and $R^{18}$ are independently selected from the group consisting of hydrogen and alkyl; and
$R^7$ and $R^{10}$ are hydroxyl.

2. The compound of claim 1, wherein the compound selectively binds to $Cu^{2+}$ in the presence of one or more different metal ions in a sample.

3. The compound of claim 1, wherein the compound does not bind to one or more of $Li^+$, $Na^+$, $Ba^{2+}$, $Sr^{2+}$, $Mg^{2+}$, $Al^{3+}$, $Ca^{2+}$, $Mn^{2+}$, $Fe^{2+}$, $Co^{2+}$, $Ni^{3+}$, $Zn^{2+}$, $Ag^+$, $Cd^{2+}$, $Hg^{2+}$ or $Pb^{2+}$.

4. The compound of claim 1, wherein the compound exhibits one or more of the following in the presence or absence of $Cu^{2+}$ ions: different visible color, different absorption spectra or different fluorescence spectra.

5. The compound of claim 1, wherein the compound exhibits an absorption spectra in the region having a wavelength of about 460 nanometers to about 1100 nanometers upon contacting $Cu^{2+}$ ions.

6. The compound of claim 1, wherein the compound exhibits an absorption spectra in the region having a wavelength of about 350 nanometers to about 400 nanometers in the absence of $Cu^{2+}$ ions.

* * * * *

UNITED STATES PATENT AND TRADEMARK OFFICE
CERTIFICATE OF CORRECTION

| | | |
|---|---|---|
| PATENT NO. | : 8,642,764 B1 | Page 1 of 1 |
| APPLICATION NO. | : 13/597323 | |
| DATED | : February 4, 2014 | |
| INVENTOR(S) | : Thimmaiah et al. | |

It is certified that error appears in the above-identified patent and that said Letters Patent is hereby corrected as shown below:

On the Title Page

On Page 2, in item (56), under "OTHER PUBLICATIONS", in Column 1,
Line 1, delete "Mettalochaperones," and insert -- Metallochaperones, --, therefor.

In the Specification

In Column 3, Line 3, delete "$R^{15}R^{16}$," and insert -- $R^{15}$, $R^{16}$, --, therefor.

In Column 4, Line 24, delete "a aromatic" and insert -- an aromatic --, therefor.

In Column 6, Line 37, delete "$Mg^+$," and insert -- $Mg^{2+}$, --, therefor.

In Column 7, Line 57, delete "$R^{15}R^{16}$," and insert -- $R^{15}$, $R^{16}$, --, therefor.

In Column 9, Line 32, delete "stiffing." and insert -- stirring. --, therefor.

In Column 10, Line 46, delete "ions, The" and insert -- ions, the --, therefor.

Signed and Sealed this
First Day of July, 2014

Michelle K. Lee
*Deputy Director of the United States Patent and Trademark Office*